United States Patent
Dlugos et al.

(10) Patent No.: US 8,337,480 B2
(45) Date of Patent: Dec. 25, 2012

(54) METHOD OF PRODUCING A BALLOON OF A BALLOON CATHETER

(75) Inventors: Tanja Dlugos, Randendingen (DE); Judith Hartwig, Grosselfingen (DE); Silke Pschibl, Rangendingen (DE)

(73) Assignee: Abbott Laboratories Vascular Enterprises Limited, Dublin (IE)

(*) Notice: Subject to any disclaimer, the term of this patent is extended or adjusted under 35 U.S.C. 154(b) by 0 days.

(21) Appl. No.: 12/064,023

(22) PCT Filed: Aug. 17, 2006

(86) PCT No.: PCT/EP2006/008118
§ 371 (c)(1),
(2), (4) Date: Aug. 19, 2008

(87) PCT Pub. No.: WO2007/020087
PCT Pub. Date: Feb. 22, 2007

(65) Prior Publication Data
US 2008/0312589 A1  Dec. 18, 2008

Related U.S. Application Data

(60) Provisional application No. 60/709,639, filed on Aug. 19, 2005.

(51) Int. Cl.
*A61M 31/00* (2006.01)
(52) U.S. Cl. .......... 604/509; 604/95.03; 604/96.01; 604/101.01; 600/115; 600/116; 264/340
(58) Field of Classification Search ............. 604/509, 604/95.03, 96.01, 101.01; 600/115, 116
See application file for complete search history.

(56) References Cited

U.S. PATENT DOCUMENTS

| | | | | |
|---|---|---|---|---|
| 4,921,478 A | * | 5/1990 | Solano et al. | 604/509 |
| 5,041,125 A | | 8/1991 | Montano, Jr. | |
| 5,049,131 A | * | 9/1991 | Deuss | 604/98.01 |
| 5,087,246 A | * | 2/1992 | Smith | 604/103.13 |
| 5,250,070 A | * | 10/1993 | Parodi | 606/194 |
| 5,267,959 A | * | 12/1993 | Forman | 604/103 |
| 5,295,995 A | * | 3/1994 | Kleiman | 606/194 |
| 5,334,146 A | * | 8/1994 | Ozasa | 604/103.06 |
| 5,342,307 A | * | 8/1994 | Euteneuer et al. | 604/103 |
| 5,370,618 A | * | 12/1994 | Leonhardt | 604/103 |
| 5,728,068 A | * | 3/1998 | Leone et al. | 604/101.01 |

(Continued)

FOREIGN PATENT DOCUMENTS
EP  1316326  6/2003
(Continued)

OTHER PUBLICATIONS

U.S. Appl. No. 60/709,639, filed Aug. 19, 2005, Dlugos et al.

*Primary Examiner* — Nicholas Lucchesi
*Assistant Examiner* — Scott Medway
(74) *Attorney, Agent, or Firm* — Workman Nydegger; Jonathan D. Feuchtwang

(57) ABSTRACT

A method of producing a balloon of a balloon catheter includes the following method steps: providing a balloon body coupled to a proximal sleeve and a distal sleeve by transitional sections extending between the balloon body and the sleeves; creating folds in at least the distal sleeve; and stabilizing at least a distal section of the folds of the distal sleeve.

20 Claims, 2 Drawing Sheets

U.S. PATENT DOCUMENTS

| | | | | |
|---|---|---|---|---|
| 5,792,415 | A * | 8/1998 | Hijlkema | 264/530 |
| 5,853,389 | A | 12/1998 | Hijlkema | |
| 5,925,058 | A * | 7/1999 | Smith et al. | 606/190 |
| 5,951,941 | A | 9/1999 | Wang et al. | |
| 6,013,055 | A * | 1/2000 | Bampos et al. | 604/103.07 |
| 6,033,380 | A * | 3/2000 | Butaric et al. | 604/103.07 |
| 6,136,258 | A * | 10/2000 | Wang et al. | 264/514 |
| 6,589,274 | B2 * | 7/2003 | Stiger et al. | 623/1.11 |
| 6,652,485 | B1 | 11/2003 | Gaudoin et al. | |
| 6,696,121 | B2 | 2/2004 | Jung, Jr. et al. | |
| 6,719,774 | B1 * | 4/2004 | Wang | 606/194 |
| 6,830,575 | B2 * | 12/2004 | Stenzel et al. | 606/108 |
| 6,863,683 | B2 * | 3/2005 | Schwager et al. | 623/1.11 |
| 7,306,616 | B2 * | 12/2007 | Eidenschink et al. | 606/194 |
| 7,309,324 | B2 * | 12/2007 | Hayes et al. | 604/96.01 |
| 7,771,447 | B2 * | 8/2010 | Kunis | 606/194 |
| 7,794,487 | B2 * | 9/2010 | Majercak et al. | 623/1.11 |
| 7,828,767 | B2 * | 11/2010 | Flanagan | 604/103.08 |
| 7,972,369 | B2 * | 7/2011 | Kaplan et al. | 623/1.12 |
| 8,083,714 | B2 * | 12/2011 | Quint | 604/103.06 |
| 2002/0138128 | A1 * | 9/2002 | Stiger et al. | 623/1.11 |
| 2004/0267195 | A1 | 12/2004 | Currlin | |
| 2005/0059989 | A1 * | 3/2005 | Eidenschink | 606/192 |
| 2006/0064064 | A1 * | 3/2006 | Jang | 604/194 |
| 2007/0088380 | A1 * | 4/2007 | Hirszowicz et al. | 606/194 |
| 2007/0167973 | A1 * | 7/2007 | Stupecky et al. | 606/192 |
| 2008/0188803 | A1 * | 8/2008 | Jang | 604/103.1 |
| 2008/0215031 | A1 * | 9/2008 | Belfort et al. | 604/500 |
| 2009/0287203 | A1 * | 11/2009 | Mazzone et al. | 606/21 |
| 2010/0030144 | A1 * | 2/2010 | Brunner et al. | 604/103.08 |

FOREIGN PATENT DOCUMENTS

| | | |
|---|---|---|
| EP | 1316326 | 5/2007 |
| WO | WO 2007/020087 | 2/2007 |

* cited by examiner

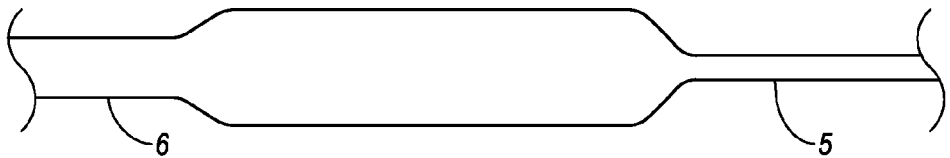

*Fig. 4*

```
┌─────────────────────────────────────────────────┐
│ Prepare A Balloon Body With A Proximate Sleeve And │
│ A Distal Sleeve With Transition Sections Extending │──11
│ Between The Balloon Body And The Respective      │
│ Sleeves                                          │
└─────────────────────────────────────────────────┘
                         │
            ┌────────────────────────────┐
            │ Reduce A Diameter Of The Distal Sleeve │──14
            └────────────────────────────┘
                         │
            ┌────────────────────────────┐
            │    Widen The Distal Sleeve    │──15
            └────────────────────────────┘
                         │
            ┌────────────────────────────┐
            │ Introduce A Filler Material Between A Guide │──16
            │    Wire Tube And The Distal Sleeve    │
            └────────────────────────────┘
                         │
        ┌────────────────────────────────────┐
        │ Creating Folds In At Least The Distal Sleeve │──12
        └────────────────────────────────────┘
                         │
    ┌────────────────────────────────────────────┐
    │ Fixing At Least A Distal Section Of The Folds Of The │──13
    │                Distal Sleeve                │
    └────────────────────────────────────────────┘
```

*Fig. 5*

METHOD OF PRODUCING A BALLOON OF A BALLOON CATHETER

FIELD OF THE INVENTION

The invention concerns a method of producing a balloon of a balloon catheter according to claim 1.

BACKGROUND OF THE INVENTION

A method of forming a balloon known from EP 1 316 326 A1 provides folds only in the conical transition sections between the balloon body and the respective neighboring sleeves.

U.S. Pat. No. 5,041,125 describes a balloon catheter having transition zones at the respective ends of the balloon body that are of fluted shape.

U.S. Pat. No. 5,853,389 describes the manufacturing process of a balloon that includes providing a mold having a cavity corresponding to an intended expanded form of the balloon member. In the molding process, the end sections of a partially manufactured balloon are twisted about an angle in relation to each other, so that helical ridges are formed in balloon transition sections between the balloon body and the sleeves.

U.S. Pat. No. 5,049,131 discloses a balloon which is formed with a fold achieved by coupling an inner wall to lines disposed parallel to the longitudinal axis of the balloon.

SUMMARY OF THE INVENTION

It is an object of the present invention to provide a method of producing a balloon of a balloon catheter having improved folding characteristics.

The solution of this object is achieved by the features of claim 1.

In detail, the method according to the present invention comprises the following method steps:

First, a balloon body is prepared having a proximal sleeve and a distal sleeve coupled thereto. Moreover, the balloon body prepared by this step has a transition section between the proximal sleeve and the balloon body and between the balloon body and the distal sleeve. All parts of the balloon manufactured according to this method step are free of any kind of folds. Methods of making such balloon bodies are described in e.g. U.S. Pat. Nos. 6,696,121 and 5,951,941.

In the next step, folds are created at least in the distal sleeve. Folds may also be created in the proximal sleeve, and it is preferred that the folds are created only in the sleeves, i.e. that no folds are created in the transition section and/or the body. Technically the folding must reach into the cone (transition section), otherwise a refolding of the balloon is not possible.

In the final step, at least a distal section or portion of the folds of the distal sleeve are fixed in position.

Although it is possible and preferred that only the sleeves are provided with folds, it is also possible to fold the entire balloon after having formed the balloon body, the transitional sections and the sleeves, so that the folds extend from the sleeves into the transitional section and the body of the balloon with the folds being fixed in their configuration, e.g. by welding, in the distal or in the proximal balloon sleeve.

The dependent claims contain other advantageous embodiments of the present invention.

Usually, a balloon manufactured according to the method of the present invention is provided with an inner tube (guide wire tube), to which the distal section of the distal sleeve is affixed to. It is preferred that the diameter of the distal sleeve is greater than the diameter of the proximal sleeve. It should be noted that the inner tube is always coupled with the distal sleeve. If it were coupled with the proximal sleeve, the balloon could not be inflated.

Moreover, it is preferred that the diameter of the distal sleeve be reduced during the production of the balloon catheter.

Alternatively, it is possible that the distal sleeve is widened after producing the balloon body, the transitional sections and the sleeves.

In another preferred embodiment, a filler material, e.g. in the form of a plastic tube, can be positioned between the guide wire tube and the distal sleeve.

It is preferred to fixedly couple said filler material or filler tube during the coupling of the folded section of the sleeve.

The present invention also concerns a balloon produced in accordance with a method according to the present application.

Further advantages and features of the present application will become apparent upon reading the following description of an exemplary embodiment with reference to the attached drawings.

BRIEF DESCRIPTION OF THE DRAWINGS

FIG. 4 shows a balloon catheter with a distal sleeve having a greater diameter than a proximal sleeve.

FIG. 5 shows an example method of producing a balloon of a balloon catheter.

DETAILED DESCRIPTION OF AN EMBODIMENT OF THE INVENTION

Figure 1:
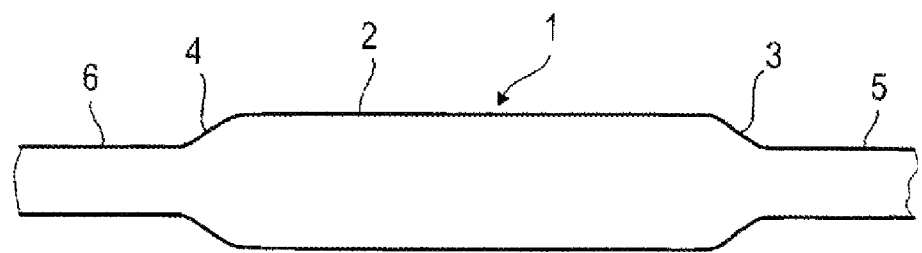
FIG. 1 shows a first step of a method according to an embodiment of the present invention.

According to the first step of a method according to an embodiment of the present invention, which is represented by the schematically simplified depiction of FIG. 1, a balloon 1 of a catheter according to an embodiment of the present invention is produced. This production step is usually carried out in a forming mold that provides a balloon body 2 of a usual cylindrical shape and two transitional sections 3 and 4, a proximal sleeve 5 and a distal sleeve 6 being connected to the respective transitional sections 3 and 4, respectively.

As shown in FIG. 1, the entire balloon 1 is entirely free of any kind of folds or flutes.

Figure 2:
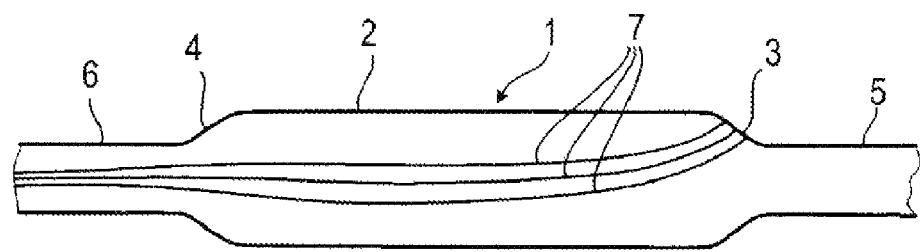
FIG. 2 shows a second step of the method of FIG. 1.

According to step 2 of the method according to the present invention (shown in an also schematically simplified depiction of FIG. 2), the balloon 1 is folded thus creating folds 7 that, in this case, run from the distal sleeve 6, the transitional section 4, the balloon body 2, the transitional section 3 to the proximal sleeve 5.

In an intermediate step, a protector can be pulled over at least the distal sleeve 6, pre-fixing folds 7.

Figure 3:
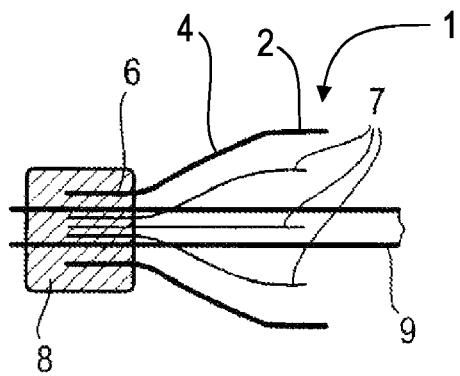
FIG. 3 shows a third step of the method of FIG. 1.

In the last method step, depicted in FIG. 3, the folds 7 are fixed at least in the distal section of distal sleeve 6, e.g. by welding, so that the sleeves can be fixed in a region of the distal sleeve 6. Welding according to this method step can encompass using hot melt. Rather than only fixing the distal region of distal sleeve 6, it is also possible to stabilize the folds extending into distal sleeve 6 over the entire length of the distal sleeve 6.

Although not depicted in the drawings, it is also possible to stabilize the folds 7 running into proximal sleeve 5 in the same manner as described herein-before.

Moreover, it is to be noted that FIG. 1 shows that the distal sleeve 6 may have a greater diameter than the proximal sleeve 5.

FIG. 4 shows a balloon catheter with a distal sleeve 6 having a greater diameter than a proximal sleeve 5.

FIG. 5 shows a method of producing a balloon of a balloon catheter. Step 11 includes preparing a balloon body with a proximal sleeve and a distal sleeve, with transition sections extending between the balloon body and the respective sleeves. Step 12 includes creating folds in at least the distal sleeve. Step 13 includes fixing at least a distal section of the folds of the distal sleeve. Step 14 may include reducing a diameter of the distal sleeve. Step 15 may include widening the distal sleeve. Step 16 may include introducing a filler material between a guide wire tube and the distal sleeve.

| Reference Numerals | |
|---|---|
| 1 | Balloon |
| 2 | Balloon body |
| 3 | Transitional section |
| 4 | Transitional section |
| 5 | Proximal sleeve |
| 6 | Distal sleeve |
| 7 | Folds |
| 8 | Welding/fixing portion |
| 9 | Guide wire tube |

The invention claimed is:

1. A method of producing a balloon of a balloon catheter comprising:
   preparing a balloon body coupled to a proximal sleeve and a distal sleeve, transitional sections extending between the balloon body and the proximal and distal sleeves, the balloon body being prepared substantially free of folds and having a generally smooth exterior surface;
   creating folds in the distal sleeve so that the folds extend from the distal sleeve into the transitional section extending between the balloon body and the distal sleeve towards the proximal sleeve; and
   stabilizing the folds in a distal section of the folds of the distal sleeve to fix the folds in the distal sleeve by pulling a protector over the distal sleeve and the folds in the distal sleeve.

2. The method according to claim 1, wherein the distal section is coupled to a guide wire tube of the balloon catheter.

3. The method according to claim 1, wherein the diameter of the distal sleeve is greater than the diameter of the proximal sleeve throughout the method.

4. The method according to claim 3, wherein the diameter of the distal sleeve is reduced during the production of the balloon catheter.

5. The method according to claim 3, wherein the distal sleeve is widened after production of the balloon.

6. The method according to claim 2, wherein a filler material is introduced between the guide wire tube and the distal sleeve.

7. The method according to claim 6, wherein the filler material is introduced during the stabilizing of the folds of the distal sleeve.

8. A balloon of a balloon catheter, comprising:
   a balloon body coupled to a proximal sleeve and a distal sleeve, transitional sections extending between the balloon body and the proximal and distal sleeves;
   wherein folds are disposed in the distal sleeve, the folds extending from the distal sleeve into the transitional section between the distal sleeve and the balloon body and towards the proximal sleeve, and
   wherein at least a distal section of the distal sleeve is stabilized by adhesive bonding or by welding on the folds in the distal sleeve to hold the folds in the distal sleeve in a fixed configuration, while the folds in the transitional section remain unfixed.

9. The balloon according to claim 8, further comprising a filler material disposed between a guide wire tube situated within the balloon catheter and the distal sleeve.

10. The balloon according to claim 9, wherein the filler material is a plastic tube.

11. The method according to claim 6, wherein the filler material is a plastic tube.

12. A method of producing a balloon of a balloon catheter comprising:
    preparing, using a mould, a balloon having a balloon body coupled to a proximal sleeve and a distal sleeve, transitional sections extending between the balloon body and the proximal and distal sleeves, the balloon being free of folds or flutes;
    creating folds in the distal sleeve of the balloon so that the folds extend from the distal sleeve into the transitional section extending between the balloon body and the distal sleeve towards the proximal sleeve; and
    fixing the folds in a distal section of the folds of the distal sleeve by adhesive bonding or by welding on the folds in the distal section to fix the folds in the distal sleeve while the folds in the transitional section remain unfixed.

13. The method according to claim 12, wherein the distal section is coupled to a guide wire tube of the balloon catheter.

14. The method according to claim 12, wherein the diameter of the distal sleeve is greater than the diameter of the proximal sleeve throughout the method.

15. The method according to claim 14, wherein the diameter of the distal sleeve is reduced during the production of the balloon catheter.

16. The method according to claim 14, wherein the distal sleeve is widened after production of the balloon.

17. The method according to claim 13, wherein a filler material is introduced between the guide wire tube and the distal sleeve.

18. The method according to claim 17, wherein the filler material is introduced during the fixing of the folds of the distal sleeve.

19. The method according to claim 12, wherein fixing the folds comprises using a protective sleeve.

20. The method according to claim 12, wherein welding comprises using hot melt.

* * * * *